US005650190A

United States Patent [19]
Buikstra et al.

[11] Patent Number: 5,650,190
[45] Date of Patent: Jul. 22, 1997

[54] HEAT-STABLE OIL-IN-WATER EMULSIONS STABILIZED BY HYDROLYZATES

[75] Inventors: Friso Pieter Martinus Buikstra, Veghel; Albertus Jacobus Martinus Maria van der Kruis, Heeze; Petrus Henricus Nicolaas van der Heijden, Veghel, all of Netherlands

[73] Assignee: Campina Melkunie, B.V., Zaltbommel, Netherlands

[21] Appl. No.: 433,838

[22] Filed: May 4, 1995

[30] Foreign Application Priority Data

May 6, 1994 [NL] Netherlands ............ 9400757

[51] Int. Cl.$^6$ ............................................. A23J 7/00
[52] U.S. Cl. ................... 426/602; 426/604; 426/656
[58] Field of Search .................... 426/601, 602, 426/605, 648, 649, 656, 654

[56] References Cited

U.S. PATENT DOCUMENTS

| | | | |
|---|---|---|---|
| 3,903,310 | 9/1975 | Buide et al. | |
| 4,411,926 | 10/1983 | Trumbetas | 426/654 |
| 4,426,395 | 1/1984 | Sakai | 426/605 |
| 4,615,900 | 10/1986 | Schenz | 426/654 |
| 4,943,389 | 7/1990 | Weete | 252/308 |
| 5,008,037 | 4/1991 | Weete | 252/314 |
| 5,024,849 | 6/1991 | Rasilewicz | 426/601 |
| 5,079,028 | 1/1992 | Wieske | 426/654 |
| 5,196,226 | 3/1993 | Sakka | 426/654 |
| 5,456,926 | 10/1995 | Hill | 426/654 |

FOREIGN PATENT DOCUMENTS

| | | |
|---|---|---|
| 0 260 573 | 3/1988 | European Pat. Off. . |
| 0 414 024 | 2/1991 | European Pat. Off. . |
| 0 546 215 | 6/1993 | European Pat. Off. . |

OTHER PUBLICATIONS

Whitaker 1972 Principles of Enzymology for the Food Sciences Marcel Dekker, Inc. New York pp. 481–489.
AR—Patent Abstracts of Japan 012, (501) (C–556), Dec. 27, 1988.

*Primary Examiner*—Carolyn Paden
*Attorney, Agent, or Firm*—Michael N. Meller

[57] ABSTRACT

The invention relates to a heat-stable oil-in-water emulsion comprising hydrolyzed protein as well as hydrolyzed lecithin having a degree of hydrolysis above 40%, to a powdery product obtained by drying an emulsion according to the invention, as well as to a dry, mixed product comprising hydrolyzed protein and hydrolyzed lecithin. The invention further relates to the use of hydrolyzed lecithin as stabilizer in oil-in-water emulsions comprising hydrolyzed protein.

25 Claims, No Drawings

HEAT-STABLE OIL-IN-WATER EMULSIONS STABILIZED BY HYDROLYZATES

BACKGROUND OF THE INVENTION

1. Field of the Invention

This invention relates to heat-stable oil-in-water emulsions which contain hydrolyzed protein. These emulsions are stabilized by a hydrolyzed glycerol derivative. The invention further relates to dried or non-dried protein hydrolyzate-containing products and foods in which an emulsion of the above-described type is used. One objective in particular is to produce baby food or a food of reduced allergenicity, using the present invention.

2. Description of the Prior Art

Proteins, in particular lactoprotein and soybean protein, are known for their function as stabilizer and/or emulsifier in oil-in-water emulsions. More particularly, lactoproteins impart to milk a stability which remains ensured both during heating, for instance in pasteurization and sterilization steps, and during storage. When proteins are subjected to hydrolysis, this good stability and emulsifying behavior declines rapidly. Thus Kühler and Stine, in their article in the Journal of Food Science 39 (1974), 379–382, described that a decline in the emulsifying behavior of proteins can be observed at a degree of hydrolysis from 5%. Furthermore, Haque and Kinsella in Milchwissenschaft 42 (1988), 236 described that when hydrolyzed protein is introduced into or present in an already formed stable emulsion, this emulsion destabilizes spontaneously.

Although other stabilizers and emulsifiers than the above-mentioned proteins are known, only a few of them are allowed in human foods. In this context reference is made to EEC directire 89/107 and the new version thereof which has been presented for approval to the European Parliament under no. C207-37 (1992). This directire regulates the use of additives in foods. In particular, it provides that in baby food only the emulsifiers lecithin (E322) and/or the partial fatty-acid ester glycerol monostearate (E471) may be used.

Lecithin is a phospholipid, more particularly a diglyceride of saturated and unsaturated fatty acids, for instance stearin, palmitin, linoleic acid and/or oleic acid, coupled to the choline ester of phosphoric acid, or a mixture of such diglycerides. Lecithin is capable of forming an eminently stable oil-in-water emulsion, in which, as a nitrogen source, principally virtually intact proteins are present. Such an emulsion also remains stable after a heating step. However, when contemplating the preparation of a food of reduced allergenicity or a different food in which protein is present for an appreciable part in hydrolyzed condition, lecithin is not satisfactory as an emulsifier/stabilizer.

The same problem arises when using the above-mentioned glycerol monostearate.

SUMMARY OF THE INVENTION

The object of the present invention is to provide an emulsifier or stabilizer which can be used without heat-stability problems in a food comprising hydrolyzed protein, in particular in baby food or in a food of reduced allergenicity.

According to the invention, these heat-stability problems are solved by the use of partially hydrolyzed lecithin as stabilizer. The use of partially hydrolyzed lecithin in an oil-in-water emulsion leads—when using conventional heating processes—to a heat-stable emulsion.

More particularly, the invention relates to the use, in oil-in-water emulsions containing hydrolyzed protein, of partially hydrolyzed lecithin having a degree of hydrolysis (DH) above 40%, preferably a DH greater than 45%, typically a DH between 50 and 80%. In this connection the term "degree of hydrolysis" is intended to refer to the percentage of converted lecithin, based on the amount of lecithin originally present. More specifically, a DH of 100% means that in 100% of the lecithin molecules one of the two fatty acid groups is lacking.

The term "partially hydrolyzed lecithin" also covers a glycerol derivative in which one of the three hydroxyl groups is replaced by the choline ester of phosphoric acid and one of the two remaining hydroxyl groups is replaced by a fatty acid residue.

DESCRIPTION OF PREFERRED EMBODIMENTS

As already stated above, lecithin is a diglyceride coupled to the choline ester of phosphoric acid. The hydrolyzed lecithins which are used according to the invention are phospholipids in which one of the two fatty acid groups, at any rate at least in a part of the lecithin molecules, is replaced by a hydroxyl group. Preferably, such a lecithin hydrolyzate is obtained by treating a lecithin of animal or vegetable origin with a phospholipase which substantially selectively breaks only one of the fatty-acid ester bonds present, such as enzymes of the classes of phospholipases A1 and A2. If we assume that the choline ester of phosphoric acid is situated at the 3-position of the glycerol unit, a phospholipase A1 splits off substantially the fatty-acid ester at the 1-position of glycerol. A phospholipase A2 provides substantially for the removal of a fatty acid tail at the 2-position of glycerol. Mixtures of phospholipases A1 and A2 can also be used, but this is not preferred because in that case a less well-defined product may arise.

According to the invention, it is essential that in the lecithin hydrolyzate mixture at least an effective fraction is present in which the phospholipid group specific for lecithin and only one fatty acid group are coupled to the glycerol residue. More particularly, according to the invention it is essential that the partially hydrolyzed lecithin product has a degree of hydrolysis of at least 40%, more preferably at least 50%, but most preferably at least 70%.

During the preparation of the lecithin hydrolyzate according to the invention, the hydrolysis of the lecithin fraction is continued so long until a product is obtained having a degree of hydrolysis of more than 40%. The degree of hydrolysis of the hydrolyzed lecithin can be determined in a conventional manner, for instance by means of HPLC or thin layer chromatography.

Although it is also possible to hydrolyze lecithin using acid, basic and/or thermal hydrolysis, enzymatic hydrolysis is preferred. The other hydrolytic techniques mentioned are not selective, so that the amount of constituents which is effective in accordance with the invention in the lecithin hydrolyzate is reduced.

Hydrolyzed lecithin can be obtained from oil-free as well as oil-containing lecithin. However, it is preferred to start from oil-free lecithin because upon hydrolysis of oil-containing lecithin undesirable byproducts (may) arise which may give rise to off-flavors of the food to be subsequently produced.

The above-described lecithin hydrolyzate is an eminent stabilizer and/or emulsifier for oil-in-water emulsions in which a protein hydrolyzate is present. An emulsion comprising protein hydrolyzate in which the stabilizer according to the invention has been used, also maintains its stability during and after a heating step, for instance in the sterilization process. Accordingly, the invention relates to a heat-stable oil-in-water emulsion comprising hydrolyzed protein as well as hydrolyzed lecithin having a degree of hydrolysis above 40%, preferably having a degree of hydrolysis above 45%, but typically having a DH between 50 and 85%.

In particular, eminent heat-stable oil-in-water emulsions are obtained when the ratio of hydrolyzed protein to hydrolyzed lecithin is between 20:1 and 1:1. In a preferred embodiment the ratio of hydrolyzed protein to hydrolyzed lecithin is in the range between 6:1 and 3:1.

In principle, any protein hydrolyzate can be present in an emulsion in which the emulsifier according to the invention is used as emulsifier or stabilizer. Typically used in such food emulsions are hydrolyzates of lactoproteins, for instance caseins and whey proteins, and, to a somewhat lesser extent, of vegetable proteins, such as soybean or wheat proteins. Such hydrolyzates are preferably obtained via enzymatic hydrolysis, but can also be prepared using other known hydrolytic techniques, such as acid, basic or thermal hydrolysis. The amount of hydrolyzation is indicated by the degree of hydrolysis (DH). In this connection, the degree of hydrolysis is defined as the percentage of the number of broken peptide bonds, based on the total number of peptide bonds in proteins. In foods of reduced allergenicity, typically hydrolyzed proteins of a DH>15% are present.

Accordingly, the invention also relates to stabilized oil-in-water emulsions in which the hydrolyzed protein is a hydrolyzate of casein, whey protein, soybean protein, wheat protein or other food proteins, which are used in mixed or unmixed form. Preferably used are protein hydrolyzates in which the hydrolyzed protein has a degree of hydrolysis of 15–70%.

In addition to the partially hydrolyzed protein fraction, the emulsion stabilized with the lecithin hydrolyzate according to the invention can contain conventional food elements, such as carbohydrates, fats and micronutrients, for instance minerals and vitamins, in such a manner that the eventual food product is suitable as a special food. The term "special food" includes inter alia hypoallergenic and lesser-allergenic foods and baby food, whether or not used as drip feed, parenteral food, medicinal food, sports food, etc.

In the context of the present invention, conventional fats that can be mentioned are: sunflower oil, corn oil, soybean oil and so-called MCT oil (medium-chain triglycerides). In practice, in special foods frequently use is made of fat mixture having a SFA:MUFA:PUFA ratio of 1:1:1, the abbreviations respectively standing for "saturated fatty acids", "monounsaturated fatty acids" and "polyunsaturated fatty acids". In a preferred embodiment the fatty fraction in the emulsion is in the range of 0.5–40% by weight.

The invention further relates to a method for preparing a stable oil-in-water emulsion comprising hydrolyzed protein, in which, as stabilizer, hydrolyzed lecithin according to the invention is used.

For the preparation of the oil-in-water emulsions stabilized with the lecithin hydrolyzate according to the invention, conventional methods can be used. These methods will at least partly depend on the final product contemplated and the ingredients therefor.

Thus it is possible to start from a pre-emulsion, but this step is not essential. The emulsion according to the invention can also be prepared in the presence of all ingredients.

If use is made of a lecithin hydrolyzate which is oil-free, then it is dispersed in a conventional manner in a part of the water fraction of the eventual emulsion. Preferably, this dispersing step is carried out at a slightly elevated temperature, for instance at 60° C. Thereupon the fat fraction is introduced into the aqueous lecithin hydrolyzate dispersion and dispersed therein using, for instance, a fast-rotating mixing gear. The thus obtained pre-emulsion can then be homogenized at a temperature of about 70° C. by methods known to those skilled in the art. Thereafter any other ingredients of the formulation, in particular hydrolyzed protein, optionally also carbohydrates, minerals, etc., and the residual portion of the water fraction can be added.

Starting from an oil-containing lecithin hydrolyzate, this hydrolyzate will first be mixed with the fat or oil fraction of the emulsion to be prepared. Then a part of the water fraction is added to this mixture, after which a pre-emulsion can be prepared again.

According to the invention, thin-fluid as well as concentrated or thick emulsions can be prepared. The thin-fluid emulsions may for instance possess a solids content of 12 to 15%, while the concentrated emulsions have a solids content of up to about 50%. As a rule, the emulsion in a more or less thin-fluid form will be suitable as an instant food, whereas more concentrated emulsions often have to be diluted before use. Further, for the preparation of dried emulsion preparations, as starting material often more concentrated emulsions are used.

The stable thin-fluid emulsion can be sterilized while maintaining a desired stability and then be thickened to a solids content of about 40 to 50%. Such a concentrated emulsion can be suitably dried after a second homogenization step.

The invention also comprises a powdery product obtainable by drying an emulsion according to the invention.

Furthermore, the invention relates to a dried mixed product of hydrolyzed protein and hydrolyzed lecithin. Such a product can be used for the preparation of emulsions according to the invention. This product has as an advantage that it is well soluble or dispersible, which accelerates the formation of a desired emulsion. Additional advantages are that the consumer, depending on his diet or preference, can compose his own specific food preparation and that a dry product has a longer shelf life than does an emulsion. This dried mixed product can be prepared by dry-mixing a dried protein hydrolyzate and a dried lecithin hydrolyzate. Preferably, however, both hydrolyzates are mixed in an aqueous phase and then dried. The drying step can be carried out by conventional techniques, such as spray-drying, freeze-drying, or roller-drying. A wet-mixed mixed product is preferred because such a product does not unmix or unmixes less rapidly. The ratio of the protein hydrolyzate to the lecithin hydrolyzate may vary depending on the final use of this mixed product, but will typically be in the range of 20:1–1:1.

Finally, the invention relates to the use of the above-defined hydrolyzed lecithin product as stabilizer and/or emulsifier in oil-in-water emulsions which comprise hydrolyzed protein.

The invention will now be further explained and illustrated in and by the following examples.

EXAMPLE 1

500 g lecithin (Sternprime N-10 Top, supplied by the firm of Stern; 65% acetone-insoluble material) was defatted by means of an extraction with acetone. Thereupon the product was dried at a temperature of 40° C. at a reduced pressure (0.1 atm.).

200 g of the oil-free fraction was suspended in 2 l water and, with continuous stirring, brought to a temperature of 55° C. Thereupon 10 g calcium chloride was added and the pH was adjusted to 9.0 using sodium hydroxide. The enzymatic hydrolysis was started up by adding 2.0 ml 10,000 IU/ml phospholipase A2 (derived from hog pancreas, Lecitase 10 L, Novo Industries, Denmark). The hydrolysis was continued for 2 hours at 55° C., whereby a DH of 69% was achieved, and after which the enzyme was deactivated by adding 5 ml Neutrase (derived from *B. subtilis*, Novo Industries, Denmark) with simultaneous lowering of the pH to 7.0 using hydrochloric acid. After an incubation time of 1 hour, the whole was heated to 95° C. Insoluble material was removed by filtration and the hydrolyzed product was dried by means of spray-drying.

EXAMPLE 2

In the manner described in Example 1, though with adjustment of the incubation time of the phospholipase, lecithin hydrolyzates of a DH of 35% and 52% were prepared.

Thereupon thin-fluid emulsions were prepared from oil-free lecithin (degrees of hydrolysis 0, 35, 52 and 69%) and protein hydrolyzate. Used as protein hydrolyzate were casein hydrolyzate having a DH of 6, 20 and 65% (respectively, MPH-6 of DMV International, Netherlands, Dellac CE90GM and Dellac CE80PS, both from Deltown Specialties, USA) and whey protein hydrolyzate having a DH of 18 and 60% (Dellac LE80BM and Dellac LE80PS, both from Deltown Specialties, USA). Further, fats, carbohydrates and minerals were added to this emulsion. The complete compositions are shown in Table 1.

TABLE 1

| Composition oil-in-water emulsions | |
|---|---|
| Hydrolyzed protein* | 1.7% |
| Hydrolyzed lecithin** | 0.5% |
| Corn oil | 3.6% |
| Lactose | 7.0% |
| Minerals | |
| Calcium | 670 mg/l |
| Sodium | 265 mg/l |
| Potassium | 690 mg/l |
| Magnesium | 68 mg/l |
| Phosphorus | 375 mg/l |
| Chloride | 595 mg/l |
| balance water | |

*either casein protein hydrolyzate of 6%, 20% and 65% DH, respectively, or whey protein hydrolyzate of 18% and 60% DH, respectively.
**Degree of hydrolysis 0-35-52-69%, respectively.

More particularly, 5 g of the lecithin was introduced into 300 ml water of 60° C. Using a fast-rotating mixing apparatus (Waring Blendor CB-6), 36 g corn oil was dispersed in the obtained dispersion. Thereupon the obtained pre-emulsion was homogenized in a Rannie laboratory homogenizer (2×250 bar; 70° C.). After cooling to room temperature, the other ingredients were added. The obtained emulsions were sterilized at 121° C. for 15 minutes in closed 100 ml glass flasks (filling level about 65–70 mm; 65–70 ml emulsion).

After a storage period of, respectively, 24 hours and 2 months at room temperature, the emulsions were evaluated as to cream line, serum separation and sediment.

Table 2 shows the results. It is noted here that the term "stable" is intended to mean the following. An emulsion is qualified as "stable" if the height of the cream layer and the serum layer is not greater than 10 mm and these layers allow ready re-mixing to form a smooth emulsion without a collar of cream adhering to the wall.

Table 2 shows that the use of a lecithin hydrolyzate having a degree of hydrolysis of 35% does not yield stable oil-in-water emulsions (non-stable emulsions are designated by "–"). Emulsions in which a lecithin hydrolyzate is used having a DH of 52% show a satisfactory stability for a short storage period. The use, as a stabilizer, of a lecithin hydrolyzate having a DH of 69% yields emulsions which are also eminently stable for longer storage periods.

TABLE 2

| | | Evaluation of oil-in-water emulsion | | | | | |
|---|---|---|---|---|---|---|---|
| | | Stability after 24 hours | | | Stability after 2 months | | |
| Lecithin | Hydrolyzates | Cream line in mm | Serum separation in mm | Sediment in mm | Cream line in mm | Serum separation in mm | Sediment in mm |
| DH = 0 | cph DH 6% | — | — | — | — | — | — |
| " | cph DH 20% | — | — | — | — | — | — |
| " | cph DH 65% | — | — | — | — | — | — |
| " | wph DH 18% | — | — | — | — | — | — |
| " | wph DH 60% | — | — | — | — | — | — |
| DH = 35 | cph DH 6% | — | — | — | — | — | — |
| " | cph DH 20% | — | — | — | — | — | — |
| " | cph DH 65% | — | — | — | — | — | — |
| " | wph DH 18% | — | — | — | — | — | — |
| " | wph DH 60% | — | — | — | — | — | — |
| DH = 52 | cph DH 6% | 10 | >2 | 3 | — | — | — |
| " | cph DH 20% | 7 | 5 | 0 | — | — | — |
| " | cph DH 65% | 3 | 2 | 0 | — | — | — |
| " | wph DH 18% | 2 | 2 | 0 | — | — | — |

TABLE 2-continued

| | | Evaluation of oil-in-water emulsion | | | | | |
|---|---|---|---|---|---|---|---|
| | | Stability after 24 hours | | | Stability after 2 months | | |
| Lecithin | Hydrolyzates | Cream line in mm | Serum separation in mm | Sediment in mm | Cream line in mm | Serum separation in mm | Sediment in mm |
| " | wph DH 60% | 3 | 3 | 0 | — | — | — |
| DH = 69 | cph DH 6% | 5 | 0 | 7 | 13 | 0 | 13 |
| " | cph DH 20% | 0 | <1 | 0 | 7 | 5 | 0 |
| " | cph DH 65% | 1 | <1 | 0 | 8 | 8 | 0 |
| " | wph DH 18% | 0 | 0 | 0 | 7 | 7 | 0 |
| " | wph DH 60% | 0 | <1 | 0 | 8 | 5 | 0 |

— = not stable
cph = casein protein hydrolyzate
wph = whey protein hydrolyzate.

EXAMPLE 3

Ten thin-fluid oil-in-water emulsions were prepared on the basis of oil-containing hydrolyzed lecithin (DH 0 and 35%, respectively) and hydrolyzed protein (casein hydrolyzate 6, 20 and 65% and whey protein hydrolyzate 18 and 60%). These basic ingredients were supplemented with fat, carbohydrates and minerals to form a thin-fluid baby food. Table 1 gives the complete formulation. In the preparation the lecithin hydrolyzate was mixed with the fat. This mixture was pre-emulsified with a part of the water at 60° C. Thereupon, analogously to Example 2, homogenization took place. Thereafter the other ingredients were added. The emulsions were sterilized and evaluated analogously to Example 2. Table 3 shows the results.

The thus obtained oil-in-water emulsion was bottled in 100 ml glass flasks (65-70 ml emulsion) and thereupon sterilized at 121° C. for 15 minutes. The stability of the emulsion was evaluated after 24 hours and after 2 months as to cream line, serum separation and sediment formed.

TABLE 4

| | after 24 hours | after 2 months |
|---|---|---|
| Cream line | 1 mm | 6 mm |
| Serum separation | <1 mm | 7 mm |
| Sediment | absent | absent |

This manner of emulsifying therefore provides stable emulsions as well.

TABLE 3

| | | Stability after 24 hours | | | Stability after 2 months | | |
|---|---|---|---|---|---|---|---|
| Lecithin | Hydrolyzates | Cream line in mm | Serum separation in mm | Sediment in mm | Cream line in mm | Serum separation in mm | Sediment in mm |
| DH = 0 | cph DH 6% | — | — | — | — | — | — |
| " | cph DH 20% | — | — | — | — | — | — |
| " | cph DH 65% | — | — | — | — | — | — |
| " | wph DH 18% | — | — | — | — | — | — |
| " | wph DH 60% | — | — | — | — | — | — |
| DH = 35 | cph DH 6% | — | — | — | — | — | — |
| " | cph DH 20% | 3 | 2 | 0 | — | — | — |
| 2 | cph DH 65% | 2 | 7 | 0 | — | — | — |
| 2 | wph DH 18% | 3 | 2 | 0 | — | — | — |
| 2 | wph DH 60% | 3 | 5 | 0 | — | — | — |

— = non-stable

EXAMPLE 4

An oil-in-water emulsion was prepared, starting from a hydrolyzed oil-free lecithin product (DH=69%) and a whey protein hydrolyzate (DH=18%). The other ingredients were dispersed in water of 60° C. by means of a fast-rotating mixing apparatus and thereupon homogenized in a homogenizer (type Rannie) at 70° C. (1×100, 2×250 bar). After cooling to room temperature, the pH was adjusted to 7.0 using a potassium hydroxide solution.

EXAMPLE 5

In the standard formulation of Example 2, 0.1%, 0.36% and 0.5% by weight of hydrolyzed oil-fat-free lecithin (DH=69%) was used. As protein hydrolyzate, whey protein hydrolyzate of a DH=18% was chosen. The oil-in-water emulsions were prepared as indicated in Example 2.

The obtained emulsions were evaluated after 24 hours' and 2 months' storage at 20° C. Table 5 below gives the results.

TABLE 5

| Lecithin DH = 69% | Stability after 24 hours | | | Stability after 2 months | | |
|---|---|---|---|---|---|---|
| | Cream line in mm | Serum separation in mm | Sediment in mm | Cream line in mm | Serum separation in mm | Sediment in mm |
| 0.1% | 5 | 5 | 0 | 9 | 62 | 0 |
| 0.36% | 0 | <1 | 0 | 8 | 6 | 0 |
| 0.5% | 0 | 0 | 0 | 7 | 7 | 0 |

A dosage of 0.1% gives a less good stability.

EXAMPLE 6

According to this Example, concentrated oil-in-water emulsions (solids about 45%) are prepared.

The basic formulation is:

Protein hydrolyzate 5.4%

(Hydrolyzed) lecithin 1.9%

Corn oil 12.6%

Carbohydrates 25.6%

Water 54.5%

As protein hydrolyzate, either hydrolyzed whey protein (DH=18 and 60%) or hydrolyzed casein protein (DH=6, 20 and 65%) was chosen.

As lecithin, either oil-free lecithin (DH=0, 20 and 69%) or oil-containing lecithin (DH=0 and 35%) was used.

First, as in Example 2, a pre-emulsion was prepared, using lecithin, water and fat. A part of the pre-emulsion was pasteurized at 80° C. for 30 minutes. This showed that no stable pre-emulsion could be obtained with non-hydrolyzed, oil-containing lecithin.

To the non-pasteurized stable emulsion were added the other ingredients of the formulation (carbohydrates, protein hydrolyzate). These oil-in-water emulsions were pasteurized at 80° C. for 30 minutes in a closed 100 ml flask.

The emulsions containing hydrolyzed lecithin were found to be stable, in contrast to the emulsions with non-hydrolyzed lecithins. With the oil-containing 35%-DH lecithin emulsions, stability was just sufficient. Sixty-nine percent-DH lecithin gave highly stable emulsions, also upon storage longer than 24 hours. It was observed that a casein protein hydrolyzate (DH=6%) gave no stable emulsions. The stable emulsions were dried (freeze-dried). These dried emulsions were well reconstitutable in water in the typical concentration of about 12% solids.

EXAMPLE 7

An oil-in-water emulsion was prepared, using oil-free lecithin hydrolyzate (DH=69%) and hydrolyzed whey protein (DH=18%). Table 6 below gives the formulation:

TABLE 6

| Whey protein hydrolyzate, DH = 18% | 5.4% |
|---|---|
| Lecithin, DH = 69% | 1.9% |
| Corn oil | 12.6% |
| Lactose | 15.4% |
| Maltodextrin | 5.1% |
| Saccharose | 5.1% |
| Water | 54.5% |

The lecithin hydrolyzate was dispersed in water of 50° C. Thereupon the fat was pre-emulsified therein using a fast-rotating mixing device. Thereupon all other dry ingredients were introduced into the pre-emulsion. This dispersion was homogenized in a Rannie homogenizer (100 bar, 50° C.) and adjusted to a pH value of 6.9 using a KOH solution. A part of the emulsion was then dried, a part was pasteurized (30 minutes, 80° C.) and a part was not further treated.

After 24 hours the stability of the last two emulsions was evaluated. Both the non-pasteurized and the pasteurized emulsion showed a slight cream line (about 7 mm), hardly any serum separation and no sediment.

The freeze-dried emulsion could be well rehydrated to an emulsion having a solids content of 12%.

EXAMPLE 8

An oil-in-water emulsion was prepared from substantially oil-free lecithin (DH=69%) and hydrolyzed whey protein (DH=18%) and water. Table 7 below gives the formulation:

TABLE 7

| Whey protein hydrolyzate, DH = 18% | 1.7% |
|---|---|
| Lecithin, DH = 69% | 0.5% |
| Corn oil | 3.6% |
| Lactose | 4.2% |
| Maltodextrin | 1.4% |
| Saccharose | 1.4% |
| Water | 87.2% |

The hydrolyzed lecithin was dispersed in the water of 50° C. The fat was pre-emulsified in this suspension using a fast-rotating mixing device. Thereupon the other ingredients of the formulation were added in dry form. The pre-emulsion was homogenized using a Rannie homogenizer (2×250 bar, 70° C.). The pH was adjusted to 7.0 with sodium hydroxide. This emulsion was sterilized at 121° C. for 15 minutes and thereupon thickened until a solids content of 50% was obtained. This emulsion was again homogenized (1×100 bar, 65° C.) and pasteurized at 80° C. for 1 minute, followed by freeze-drying.

The thus obtained dried emulsion was well dispersible in water in a concentration of 13%.

The stability of the rehydrated emulsion was evaluated 24 hours after the preparation. A cream line of less than 1 mm, a serum separation of less than 1 mm and hardly any sediment were found.

EXAMPLE 9

1,600 kg powdery whey protein hydrolyzate (DH=18%) was dry-mixed in an industrial mixer (Lödige mixer) with 400 kg oil-free hydrolyzed lecithin (DH=69%). The grain size distribution of the two hydrolyzates was practically the same ($d_{50}$ about 50 μm), so that no unmixing occurred. Starting from this mixture, an emulsion was made. To that end, 24 g of the mixture was suspended in 500 ml water of 60° C. In this suspension 36 g corn oil was suspended and thereupon homogenized by means of a Rannie laboratory homogenizer (2×250 bar; 70° C.). Thereafter 70 g milk sugar and 3 g of a mineral mix (see Example 3) were added and finally supplemented with water to 1 liter. The obtained emulsions were sterilized at 121° C. for 15 minutes and bottled in closed 100 ml flasks.

The emulsions were stored for 2 months at room temperature and thereupon evaluated for stability. The cream line, like the serum separation, was not more than 7 mm. These emulsions were of good stability.

EXAMPLE 10

100 kg of a hydrolyzed (18% DH) whey protein-containing suspension (solids=40%) was mixed with 100 kg hydrolyzed (69% DH) oil-free lecithin emulsion (solids=10%) and threreupon homogenized at 50 bar and 70° C. This mixture was dried by means of a spray drier at an input air temperature of 180° C. and an output air temperature of 96° C.

Analogously to Example 9, an emulsion was prepared. This emulsion too was stable upon a storage period of 2 months at room temperature.

We claim:

1. A heat-stable emulsifying agent for use in oil-in-water emulsions comprising hydrolyzed protein as well as hydrolyzed lecithin wherein the hydrolyzed lecithin has a degree of hydrolysis above 40%.

2. An emulsifying agent according to claim 1, wherein the ratio of hydrolyzed protein to hydrolyzed lecithin is between 20:1 and 1:1.

3. An emulsifying agent according to claim 2, wherein the ratio of hydrolyzed protein to hydrolyzed lecithin is between 6:1 and 3:1.

4. An emulsifying agent according to claim 2, wherein hydrolyzed protein and hydrolyzed lecithin are each present in an amount between 0.1 and 6% by weight, based on the total emulsion.

5. An emulsifying agent according to claim 2, wherein the hydrolyzed protein is a hydrolyzate of a food protein selected from the group consisting of casein, whey protein, soybean protein, wheat protein, and mixtures thereof.

6. An emulsifying agent according to claim 2, wherein the hydrolyzed protein has a degree of hydrolysis of 15 to 70%.

7. A powdery product obtained by drying an emulsifying agent according to claim 2.

8. An emulsifying agent according to claim 1, wherein the ratio of hydrolyzed protein to hydrolyzed lecithin is between 6:1 and 3:1.

9. An emulsifying agent according to claim 8, wherein hydrolyzed protein and hydrolyzed lecithin are each present in an amount between 0.1 and 6% by weight, based on the total emulsion.

10. An emulsifying agent according to claim 8, wherein the hydrolyzed protein is a hydrolyzate of a food protein selected from the group consisting of casein, whey protein, soybean protein, wheat protein, and mixtures thereof.

11. An emulsifying agent according to claim 8, wherein the hydrolyzed protein has a degree of hydrolysis of 15 to 70%.

12. A powdery product obtained by drying an emulsifying agent according to claim 8.

13. An emulsifying agent emulsion according to any claim 1, wherein hydrolyzed protein and hydrolyzed lecithin are each present in an amount between 0.1 and 6% by weight, based on the total emulsion.

14. An emulsifying agent according to claim 13, wherein the hydrolyzed protein is a hydrolyzate of a food protein selected from the group consisting of casein, whey protein, soybean protein, wheat protein, and mixtures thereof.

15. An emulsifying agent according to claim 13, wherein the hydrolyzed protein has a degree of hydrolysis of 15 to 70%.

16. A powdery product obtained by drying an emulsifying agent according to claim 13.

17. An emulsifying agent according to claim 1, wherein the hydrolyzed protein is a hydrolyzate of a food protein selected from the group consisting of casein, whey protein, soybean protein, wheat protein, and mixtures thereof.

18. An emulsifying agent according to claim 17, wherein the hydrolyzed protein has a degree of hydrolysis of 15 to 70%.

19. A powdery product obtained by drying an emulsifying agent according to claim 17.

20. An emulsifying agent according to claim 1, wherein the hydrolyzed protein has a degree of hydrolysis of 15 to 70%.

21. A powdery product obtained by drying an emulsifying agent according to claim 20.

22. A powdery product obtained by drying an emulsifying agent according to claim 1.

23. A dry, mixed product comprising hydrolyzed protein and hydrolyzed lecithin having a degree of hydrolysis above 40%.

24. An oil-in-water emulsifying agent comprising hydrolyzed protein, wherein hydrolyzed lecithin having a degree of hydrolysis above 40% is used as a stabilizer.

25. A method for preparing a stable oil-in-water emulsion comprising the steps of:
   a) providing an oil fraction, and
   b) a water fraction,
   c) adding hydrolyzed lecithin having a degree of hydrolysis above 40%, to the oil fraction if the hydrolyzed lecithin contains oil, or to the water fraction if the hydrolyzed lecithin is oil-free and dispersing the oil fraction in the water fraction, and
   d) adding with agitation, hydrolyzed protein to the oil-in-water emulsion resulting in an oil-in-water emulsion comprising hydrolyzed protein and hydrolyzed lecithin.

* * * * *